United States Patent
del Rosario Guadalupe Vega y Saenz de Miera et al.

(10) Patent No.: US 11,721,233 B2
(45) Date of Patent: Aug. 8, 2023

(54) DEVICE FOR THE USE OF VESTIBULAR GALVANIC STIMULATION FOR PILOT TRAINING AND THE CORRECTION OF THE POSITION AND SIGHT FIXATION IN MICROGRAVITY

(71) Applicant: BENEMÉRITA UNIVERSIDAD AUTÓNOMA DE PUEBLA, Puebla (MX)

(72) Inventors: María del Rosario Guadalupe Vega y Saenz de Miera, Puebla (MX); Enrique Soto Eguibar, Puebla (MX); Jorge Luis Gordillo Domínguez, Puebla (MX); Adriana Cristina Pliego Carrillo, Puebla (MX); Vladimir Aleksandrov, Puebla (MX); Tamara Alexandrova, Puebla (MX); Octavio González Petlacalco, Puebla (MX); Baruc Zago Mazzocco, Puebla (MX); Francisco Javier Mendieta Jiménez, Mexico City (MX)

( * ) Notice: Subject to any disclaimer, the term of this patent is extended or adjusted under 35 U.S.C. 154(b) by 538 days.

(21) Appl. No.: 16/870,628

(22) Filed: May 8, 2020

(65) Prior Publication Data
US 2020/0357298 A1   Nov. 12, 2020

(30) Foreign Application Priority Data

May 9, 2019  (MX) .................... MX/a/2019/005432

(51) Int. Cl.
*G09B 9/02* (2006.01)
*A61N 1/36* (2006.01)
*G09B 9/08* (2006.01)
*G06F 3/01* (2006.01)

(52) U.S. Cl.
CPC ........... *G09B 9/02* (2013.01); *A61N 1/36036* (2017.08); *A61N 1/3603* (2017.08); *G06F 3/012* (2013.01); *G06F 3/013* (2013.01); *G09B 9/08* (2013.01)

(58) Field of Classification Search
None
See application file for complete search history.

(56) References Cited

U.S. PATENT DOCUMENTS

| 8,855,774 B2 | 10/2014 | Soto Eguibar et al. |
| 2017/0274211 A1* | 9/2017 | Galea .................. A61N 1/0456 |

FOREIGN PATENT DOCUMENTS

RU   2500375   12/2013

* cited by examiner

*Primary Examiner* — Michael W Kahelin
(74) *Attorney, Agent, or Firm* — Ryder, Mazzeo & Konieczny LLC; Joseph M. Konieczny, Sr.

(57) ABSTRACT

A method is proposed to induce the sensation of movement in subjects in flight simulators and in cosmonauts, creating a cognitive simulation of movement through the Vestibular Electrical Stimulation. The system consists of a control unit, a function generator and a power amplifier. The device injects electric current over the mastoid process (galvanic vestibular stimulation), capable of activating the neurons of the vestibular system and inducing a movement sensation, in coordination with a flight simulation program or subject's movement in the simulator. The use of the device modifies eye movement control responses, electrically activating the vestibular-ocular, vestibulo-colic and vestibule-spinal reflexes. The main purpose of this device is to provide sensory input to enhance the experience in pilots during flight training or in microgravity.

7 Claims, 6 Drawing Sheets

DEVICE FOR THE USE OF VESTIBULAR GALVANIC STIMULATION FOR PILOT TRAINING AND THE CORRECTION OF THE POSITION AND SIGHT FIXATION IN MICROGRAVITY

FIELD OF THE INVENTION

This invention relates to a system and method for non-invasive artificial stimulation of the vestibular system of a human subject.

BACKGROUND OF THE INVENTION

Flight simulators create a virtual reality through the visual and auditory dynamic simulation of the environment, and the use of movement platforms mimicking the airplane's flight altitude. The present invention relates to systems and methods of Vestibular Galvanic Stimulation (GVS) to be used in aeronautics and cosmonautics, in pilot training in flight simulators and in space weightlessness.

The Vestibular System is formed by a set of natural biomechanical sensors located in the inner ear of human beings. In a healthy person, the vestibular system is responsible for producing the appropriate reflexes and reactions to achieve and maintain a stable position of the body, as well as to stabilize the gaze. This biomechanical system is composed of 3 semicircular canals (lateral, posterior and anterior), oriented almost orthogonally, and two otolithic organs (saccule and utricle). The semicircular canals (SCC) allow to detect angular movements of the head while the otolithic organs provide information of linear displacements (such as normal gravitational). The vestibular system generates a set of vestibule-spinal, and vestibule-colic reflexes that contribute to maintaining stable posture, vestibule-ocular reflexes related to the maintenance of visual stability and vestibule-autonomic reflexes related to vaso-vagal stability.

Extraocular muscles are the effectors of the vestibular-ocular reflexes. They contract or relax in such a way that when they receive an electrical signal, they act to move the eyes in a specific direction and in a coordinated way. The activation or deactivation of the SCC by a mechanical (or galvanic) stimulus determines, according to SCC activated, the direction of eye movement. The degree of activation of each SCC determines the direction and magnitude of eye movement. The purpose of GVS is to stimulate the SCC of the pilot to help stabilize gaze on a visual target (Reynolds and Osler, 2012). Then, for example, by having a right turn in the frontal plane of a person (and stimulating on the right side), it is expected that the anterior and posterior channels of the right side will be activated while the vertical channels on the contralateral side are deactivated. It has been established a relationship between the SCC planes and the direction of the induced movement of the eyes and head.
Galvanic Vestibular Stimulation (GVS)

As described in our previous inventions Patent MX/a/2013/007969. "Vestibular prosthesis" and U.S. Pat. No. 8,855,774 B2 "Vestibular prosthesis", GVS is a non-invasive method that depending on the characteristics of the stimulus (timing of stimulation, electrode location, current intensity and stimulus waveform), produces specific postural responses related to semicircular canals activation (angular movement sensation) or of the otolithic organs (linear displacement). The method for GVS is to apply a current from 0.5 to 2 mA, using surface electrodes of which at least one must be on the mastoid process. The stimulus causes the sensation of displacement and consequent vestibulo-ocular and postural responses. GVS produces a vestibular response without exciting other sensory inputs. When an alternating current is applied at a low frequency, the stimulus has an influence on the stabilization of the gaze, and the displacement of the eyes. On the other hand, when direct current is applied, a displacement sensation with inclination of the body is generated. Galvanic stimulation modulates the discharge of vestibular afferent neurons. The cathodic current increases the frequency of discharge of neurons, while the anodic current decreases it. Cathodic or anodic GVS affects the discharge of afferent neurons from the semicircular canals similarly to an ipsilateral angular acceleration. Our research group has developed systematic and adequately parameterized studies of the effect of the position of the electrodes, the possible combinatorial between polarities and modalities (bipolar vs unipolar) and the effect of the GVS waveform.

This work presents the development of a vestibular auxiliary device and GVS-based methods that modulate the sensation of movement in a virtual reality environment in flight simulators used for the training of aircraft pilots. Another embodiment of use of the device is in conditions of microgravity, in which GVS produces correlative response to movement and allows vestibular information input to be restored to the cosmonauts. Previous results of our research group demonstrate that this system works to modulate postural responses in normal subjects, hence its deeper characterization and its use in a group of experimental subjects that are placed on a flight simulation platform of an airplane allows to study the influence of GVS on the pilot's vestibulo-ocular reflexes, and define that GVS helps to enhance pilot's sensation of movement, simulate the overloads lived through flight simulation and improves the pilot's visual stabilization.

SUMMARY OF THE INVENTION

In this proposal, a method for vestibular galvanic stimulation (GVS) in flight aircraft pilot training is intended.

A method for vestibular galvanic stimulation (GVS) commanded by movement in cosmonauts under microgravity conditions is also intended.

BRIEF DESCRIPTION OF THE DRAWINGS

The particular characteristics and advantages of this invention, as well as other objectives of the invention, will become apparent from the following description, taken along with the attached figures, which.

3. Digital-Analog converter built with, but not restricted to, series of resistors. 4. Power stage, built with, but not restricted to, an LM358N low consumption operational amplifier. 5. Built with, but not restricted to, a Keyboard to navigate the menu. 6. Power supply built with, but not restricted to, a 5v, 12v and −12v.

Figure 3:
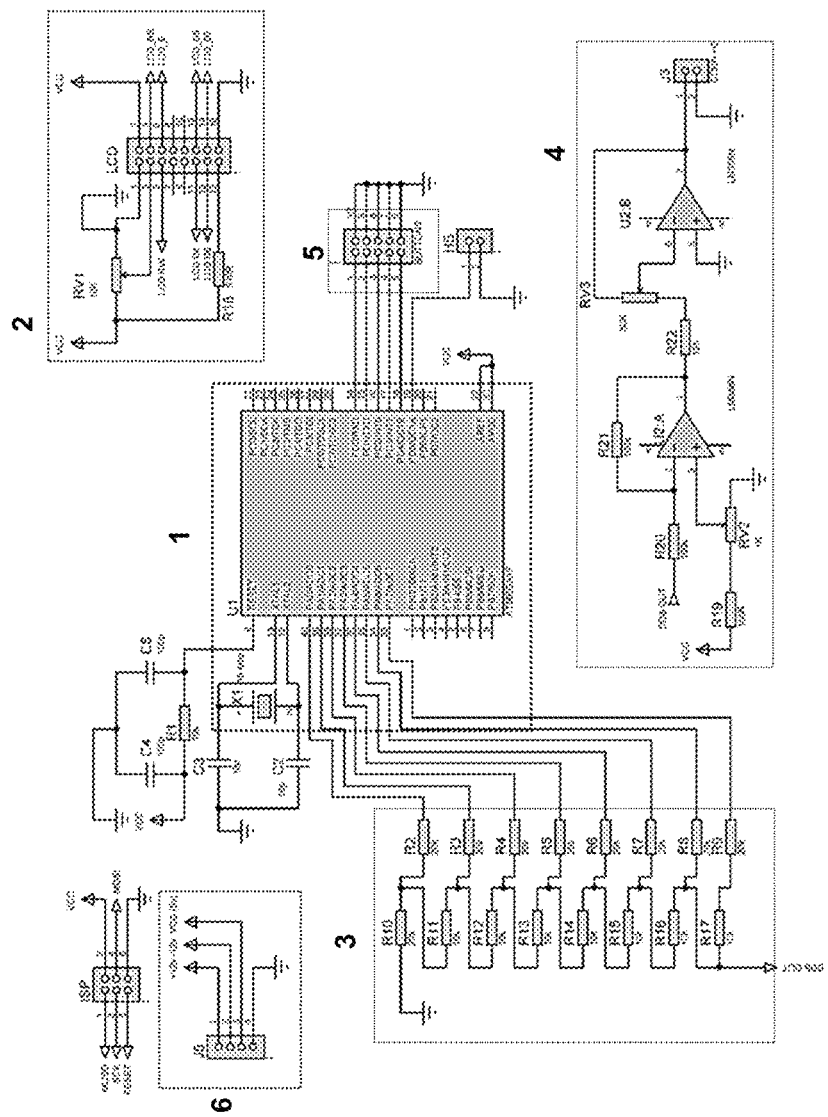
FIG. 3 illustrates a current amplifier according to this disclosure. Electronic diagram for galvanic vestibular stimulator. Basic Components including: 1. Control stage, built with, but not restricted to an ATMEGA16 Microcontroller with 16 MHz external crystal clock. 2. Display, built with, but not restricted to, a display model HD44780 2×16 LCD.
Figure 4:
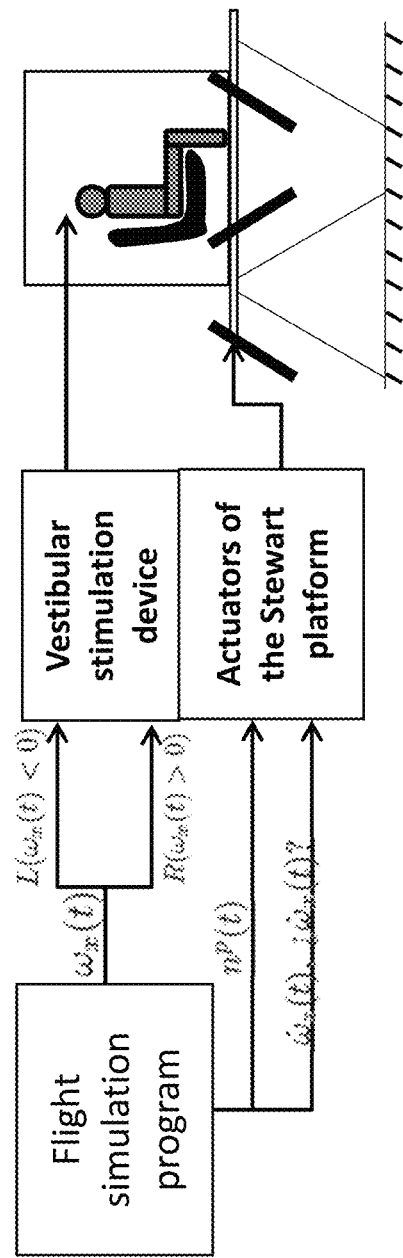

FIG. 4 illustrates an experimental setup for GVS according to this disclosure. Experimental setup for the application and study of the vestibular device. The subject sat in a cockpit on the Stewart platform that simulates the movement of an aircraft. In addition to the dynamic simulation produced by the platform, our proposal consists of additional movement induced sensation using the GVS-device as stablished according to FIG. 2 and FIG. 3.

Figure 5:
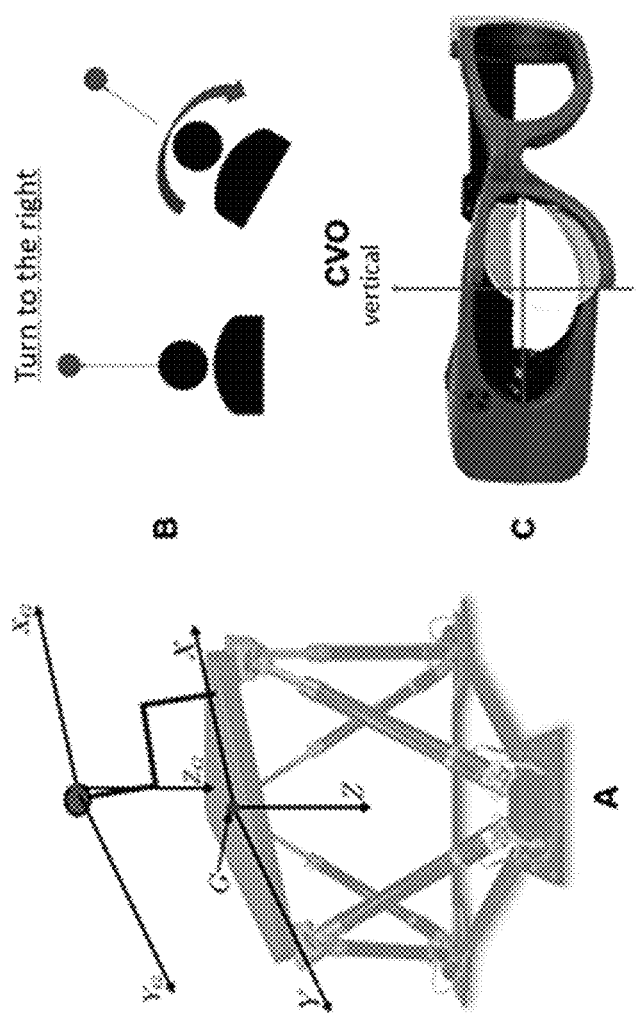

FIG. 5 illustrates an experimental recording of head and eye movements according to this disclosure. In A, configuration of the Stewart platform reference system and the pilot body reference system. In B, point target tracking by the pilot in the dynamic simulator cabin, C: system for detecting eye and reference movement in the Video Eye Camera (CVO).

Figure 6:
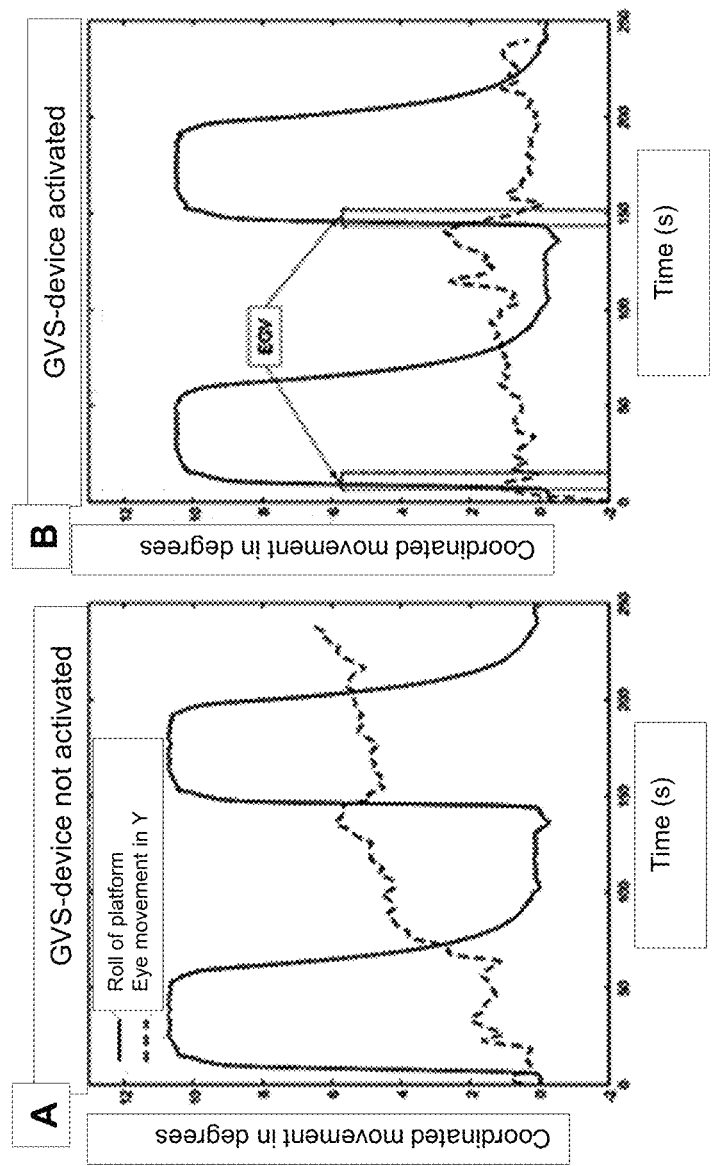

FIG. 6 illustrates registration of ocular and platform movements according to this disclosure. Recording of movement of the Stewart platform and of eye movement during coordinated platform-turn experiments. The Stewart platform (PS) movement in the direction of warping is presented in a continuous line. On the dotted line the movement of the eyes in the vertical direction. In A, the result of two platform warp under control condition (without GVS). In B, the device is active and GVS (gray box) is applied at each platform warp of the experiment. GVS significantly modified the ocular vestibule responses in the subject.

DETAILED DESCRIPTION OF PREFERRED EMBODIMENTS

Figure 1:
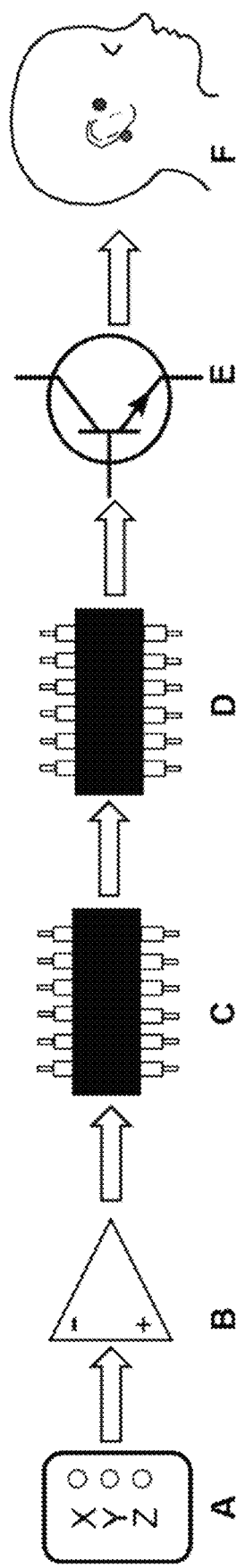
FIG. 1 illustrates a GVS device for pilots: global schematic of the proposed device. Global schematic of the proposed device. An inertial sensor, B offset adjustment, C microcontroller, D V-F converter, E Current amplifier, F Stimulation electrodes at the subject's head.
Figure 2:
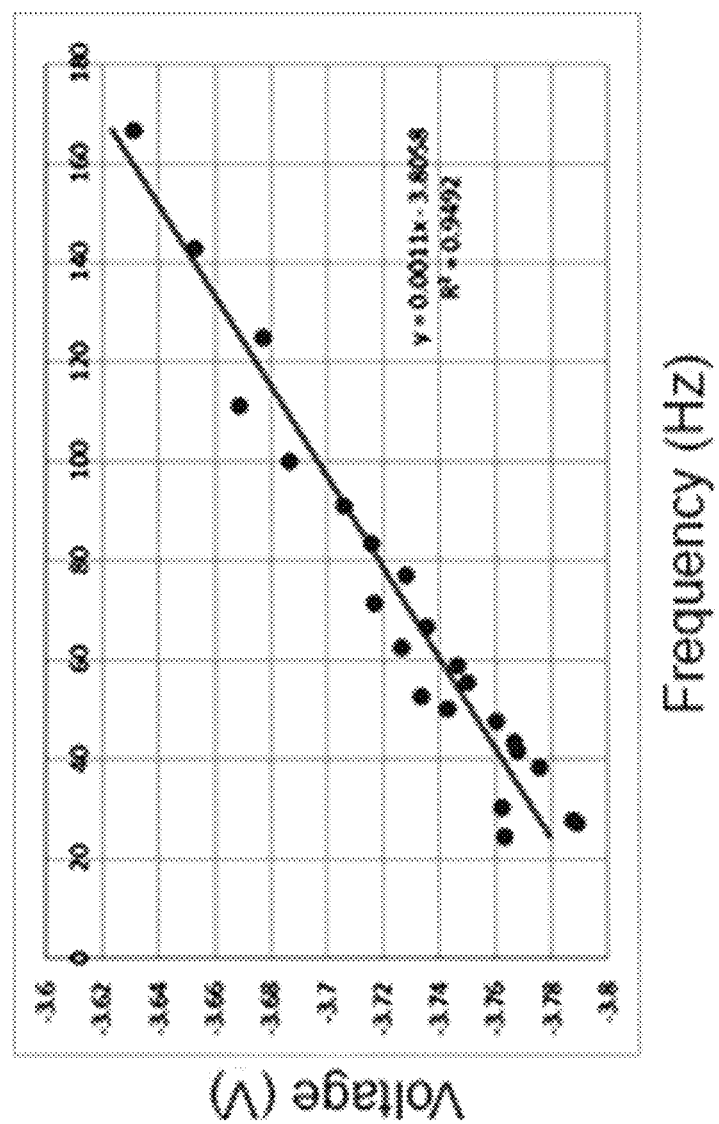
FIG. 2 illustrates a voltage-frequency curve drawn with data acquired from the system according to this disclosure. Graph of the input (accelerometer) and output (train pulse frequency) acquired from pilot training system in response to acceleration. Dots—sample data from acquisition. Solid line—linear function approximation.

The device includes the following parts as shown in FIG. 2:
- A. Inertial sensor-built with, but not restricted to, an analog inertial sensor that provides triaxial output.
- B. An offset adjustment module-built with, but not restricted to, an operational amplifier differentiator.
- C. A microcontroller that determine the mathematical function that relates input and output signals.
- D. A voltage-to-frequency converter-built with, but not restricted to, ICL8038 signal generator.
- E. A current amplifier-built with, but not restricted to, a transistor configuration that allows power signal amplification.
- F. Stimulation electrodes-built with, but not restricted to, disposable stimulation electrodes Signal Acquisition.

Inertial sensor converts acceleration, linear or angular, proportionally into voltage variations in three spatial axes. Output voltage may serve as input to a voltage to frequency converter. Particularly, we are interested in turning acceleration-voltage into a square signal whose frequency is related mathematically to input. Frequency must oscillate, but is not restricted to, natural burst frequency in afferent neurons of the vestibular system, from 80 to 200 Hz.

Offset Adjustment.

It was necessary to build an element that could move the inertial signal in reference to ground voltage. This enables a full range frequency modulation according to inertial input. The offset voltage variation determines the proportion of accelerometer signal that will be fully represented by square frequency modulated output signal.

Voltage-Frequency Curve.

A voltage-frequency curve was drawn with data acquired from the system built. Modulation range is >20 Hz and <170 Hz. Voltage range measured from the inertial sensor is from −3.8 V to −3.64 V, see FIG. 2.

In order to deliver the frequency modulated signal to stimulation electrodes, a signal current amplifier is needed. A circuit for current control and injection was developed based on this embodiment and is shown in FIG. 3, but not restricted to an ATMEGA16A programmable integrated circuit, which will function as a signal generating unit, the device was recorded with a program that contains different routines which serve to generate the required signals and select, through menu, the signal that we want at the output of this device, these signals can be: sine, square, white noise, or other of interest. The device also allows modulating the frequency of the signal using a voltage-frequency converter, which can vary between 1 Hz and 10 MHz with steps in frequencies between 1, 10, 100 and 1000 Hz. The signal obtained at the output of the control device is coupled to an electronic current amplifier. The purpose of this stage is that the signal obtained from the device has the power necessary to apply a stimulus that causes a response in the subject. In this embodiment of the invention, we use, but are not restricted to, two operational amplifiers, in a current inverter configuration. In this stage the circuit is used to implement an offset control, to select the positive or negative period of the output signal.

Since the power stage can generate a current greater than that required, this device has a current limiting circuit for current peak protection. The purpose of this circuit is to maintain current at the desired value during stimulation period, regardless variations in the load resistance (impedance or resistive value of the subject between the electrodes) and thus prevent current changes that may cause discomfort or damage to the subject receiving the stimulus. The output of the device has a customized connector to facilitate the use of sticky surface electrodes. Stimulation electrodes are made of a conductive, non-reactive, material. Adding electrolytic gel to this material forms a low impedance (resistance) interface between the device and the subject (load circuit).

In this embodiment is included, but not restricted to, a digital display that shows the stimulation signal waveform and frequency, delivered by the output of the power amplifier. Navigation through a digital menu is achieved by push-buttons of the circuit.

For pilot training, the projection of a visual flight simulation on a screen is used in combination with a Stewart platform. The latter includes actuators, whether electric or mechanical; actuators increase or decrease their length to simulate tilts about rotation planes of roll, pitch and yaw. In the experimental stage, we found that it is not feasible for the platform to make turns of more than 30° in the yaw plane. Additionally, movement speed was low due to physical limitations of the actuators.

Our proposal of a vestibular device for pilot training would cover the needs for simulation based in movement platforms, but would not be limited to these needs, because it would enhance the information perceived by pilots while training in the platform (flying simulator); Not only being the physical stimulation generated by the movements of the platform, but, besides to visual display and auditory signals, the vestibular device will deliver GVS to directly stimulate the organs of balance of the pilot.

Geometric deficiencies of the Stewart platforms to generate inclinations in the horizontal (yaw) plane depend on the configuration of its actuators, there are situations in which its movement is restricted by the limitations of platform's actuators. Such is the case of yaw rotation, carried out on the horizontal plane, around an axis perpendicular to the base of the platform.

The application of this invention is aimed for pilot training in flight simulators using a Stewart platform, but not limited to simulate flight, it will also help pilots to perceive additional accelerations to those induced by the angular motion provoked by the Stewart platform.

Regarding the use of this invention in microgravity conditions (such as in the International Space Station), the delivery of GVS magnitude and characteristics proportional to the intensity of movement of the astro- or cosmonauts will allow sensory restoration, at least partially, vestibular input related to movement will attenuate cognitive alterations that occur as a result of microgravity.

Test of the System

To demonstrate that our main goal using GVS for pilot training and control of space position is appropriate, we conducted a series of experiments with GVS on voluntary subjects in a flight simulator.

All GVS experiments were carried out taking care of the welfare of the voluntary subjects. The norms established in the Declaration of Helsinki (World Medical Association Declaration of Helsinki 2013) and the Official Mexican Standard (NOM-012-55A3-2012) for experimentation with humans were followed. An informed consent was signed, and clinical history of each voluntary subject was completed.

Voluntary subjects selected for the GVS experiments were between 18 and 30 years old (healthy without any pathology). Square pulses of 0.1 to 2 mA were applied; The electrical stimulation was injected through 1 cm diameter chlorinated silver electrodes (3M, Red Dot) placed in the mastoid process and the other electrode (reference) in the frontal region on the right side of the subject.

The subjects sat in the cockpit of a dynamic flight simulator based on a Stewart platform. The Stewart platform as a generator of angular movements is part of a dynamic flight simulator that contains a cockpit and a display screen. In the experiment, the pilot's seat, inside the cabin, was used. Simulator movement was produced by specific algorithms to mimic the flight of an aircraft. The flight path consists of a maneuver used by pilots to evade obstacles or change their course, known as coordinated turn, which consists in making the plane perform a right or left turn in the flight simulation, changing its course, then turn again in the opposite direction to the first position in order to establish and maintain a new direction. Coordinated turn is considered, as in the case of this experiment, when the warping angle, $\phi$, is non-zero (to make the rotation of the aircraft in the simulated flight environment), the angle of attack is practically zero, $\alpha \approx 0$, and the sliding angle (skidding) is zero, $\beta = 0$, speed and altitude remain constant as well.

Monopolar unilateral GVS was used, which consisted on direct current stimulation of 2 mA for 8 seconds; the cathode was connected to the right mastoid process (behind the ear) and the anode centered on the forehead of the pilot. The placement of the electrodes was done before generating the movements of the Stewart platform, ensuring that the pilots did not show any discomfort. The GVS, for the purpose of the experiments, was used to counteract the influence of mechanical stimulation introduced by the Stewart platform as shown in FIG. 4. Each subject experienced two periods of stimulation and a Control period (platform rotation without GVS).

Linear and angular movements of the head and eye of the pilot were recorded using an ICS Video Head Impulse. The equipment consists of a high resolution micro camera, micro gyroscopes and micro accelerometers all mounted on glasses, which the subject can use comfortably. This device measures with high precision ocular movements and the movement of the head of a subject. In the case of eye movements, the reference system is located inside the Ocular Video Camera (CVO) as shown in FIG. 5, so that, at all times, the horizontal and vertical deviations of the right eye are measured, regardless of the orientation of the subject's head (pilot), we can also obtain speed and acceleration by deriving them numerically.

As there is a mechanical stimulus to the right and to the left, generated by the Stewart platform, the pilot will experience, in accordance to the response of vestibular system electrical stimulation, enhancement perceptions of movement in coordination with movement will be sensed.

Three voluntary subjects participated in the execution of the experiments, and with each of them the right turn maneuver was executed three times. Briefly, the following was done in a dynamic simulator two coordinated turns to the right were made for each experiment. Stewart platform inclination is made around the X plane (warping). The pilot's head moves in coordination with the platform to the right, so the activation of the SCCs is restricted to those in the vertical orientation. A fixed point was placed on the dynamic simulator display screen, so that the pilot has to try fix his(her) gaze throughout the experiment. The pilot did not perform maneuvers and was instructed to fix gaze. GVS was applied at t=9 s after the Stewart platform began its right-turn movement. Turn maneuvers were performed in triplicate, for all pilots, GVS was applied in two of them. During the first experiment GVS was applied, in the second it was not applied, and in the third it was applied again.

Results related to eye and head movement of the pilot were obtained with the video-ocular recording camera, gyro sensors and accelerometers. The movement of the Stewart platform is shown with the solid line, while the dotted line represents the movement of the right eye on the vertical axis as shown in FIG. 6. In the first turn, the pilot seeks to follow the warping movement of the platform in an appropriate manner according to his perception (response to mechanical movement). The movement of the Stewart platform is not very fast, however, that generates in the pilot a feeling that he will continue with his right-turn movement, but he finds that the Stewart platform reaches its limit and then returns to the starting position (0°). In this case, the stability of the pilot's gaze is maintained in reference to the position recorded at the end of the first turn. In the second turn, t≈1 45 s, the pilot took the information of the previous mechanical movement to predict eye position, which is a repeated. This is an expected behavior in a healthy person.

On the right side of scheme 6 at t=9 s, the 2 mA GVS was activated for 8 s. The pilot turned his head according to the mechanical influence of the Stewart platform and unlike the first experiment, he was able to stabilize his gaze at the fixed point and it is observed that the vertical movement of the eye goes in the direction of the movement of the head, which is expected as the fixed point moves next to the cockpit. Subsequently, in the second platform turn, when GVS is applied, stabilization is sustained and manages to be maintained for the remaining time of the experiment. This allows gaze stabilization to improve because, while the mechanical stimulus is causing the pilot to lose sight of the objective (fixed dot), GVS promotes gaze stabilization. These results demonstrate that GVS can be used in pilot training since it contributes to gaze stabilization.

We propose to use GVS as a method both to generate an augmented reality experience and to contribute to pilot training and its application in gaze stabilization of pilots in flight and in microgravity conditions.

Our proposal is to use a portable device using GVS, during the training process of pilots in flight simulators, to generate tilt and virtual displacement sensations, coupled with the physical and technical capabilities of the simulators.

Likewise, it is proposed to make use of the GVS to counteract the mechanical effects (unwanted displacement) of eyeballs, to stabilize gaze during flight.

We also propose to use the device during orbital flight in cosmonauts (in this case, GVS depends on the output of ultrasensitive sensors (accelerometers and gyroscopes) to generate sensations of tilt and virtual displacements.

Potential Advantages of this Patent

The device, according to this disclosure, can be used for the training of aircraft pilots, due to its influence on the vestibular system and gaze stabilization.

The device, according to this disclosure, can also be used for training and to improve the execution and stability of cosmonauts in orbital flight and in microgravity.

The device, according to this disclosure, is based on the application of GVS which is a non-invasive electrical stimulation method (no implants required), of which no long-term adverse effects have been reported. Since it directly stimulates reflex pathways (vestibule-ocular and vestibule-spinal), it does not require learning by users to interpret the stimulus. In addition, its prolonged use does not produce adaptation, so it will have the same effect on users regardless of how many times the device has been previously used.

Comparison with Other Technological Developments or Related Innovations

There are proposals in the literature to use GVS as a tool to generate augmented reality of movement in subjects in virtual environments such as video games. One proposal is that of Aoyama, which, by placing electrodes on the atrial periphery, generates realistic acceleration sensations. This method was called: walk with GVS (GVS RIDE in English); The idea is to use both the GVS and augmented reality headset in combination with video games (Aoyama et al., 2015; Aoyama 2017).

Competition Analysis

In addition to the characteristics described above, the Stewart platform has the limitation of generating low speed tilts, mainly in the Z plane (yaw inclination), due to the characteristics of the actuators that produce movement. An important factor that increases the potential of our methodological proposal is that although galvanic stimulation is being used in research with the objective of generating knowledge linked to the vestibular system, we propose using stimulation to modulate spatial orientation, whether with test pilots or in microgravity. Other methods for vestibular stimulation:

Currently there are other methods of vestibular stimulation, one of them is transcranial magnetic stimulation, which is still under investigation. It should be noted that GVS devices, both in the market and research, are usually portable and easy to transport and require low energy consumption compared to magnetic stimulators, which is an advantage if used in confined spaces.

From previous investigations using magnetic stimulation, side effect ranging from dizziness to sensation of eye rotation have been reported, according to the power of the applied magnetic flow. This flow can be between 1 and 3 Tesla or more, with 4 Tesla being the maximum applied to human beings. It is not yet known exactly how the magnetic flux influences the vestibular system. Some studies indicate that Lorentz's strength, or magnetic field strength deflects the ionic currents of the hair cells, creating a sensation of rotation. If this force is strong enough, it can cause eye movements. In cases where the subject has vestibular damage, eye movements do not occur.

The invention claimed is:

1. An electronic device for low intensity vestibular galvanic stimulation (EGV) ≤2 mA for pilot training, that includes:
   i) a programmable integrated circuit containing three programmed routines: sinusoid, square and white noise;
   ii) a converter with a plurality of simple resistors wherein resistors R2, R3, R4, R5, R6, R7, R8 and R9 are connected directly to a plurality of pins PA0, PA1, PA2, PA3, PA4, PA5, PA6 and PA7 of a port A of the programmable integrated circuit;
   iii) a low consumption current amplifier;
   iv) a screen-display;
   v) a keyboard directly connected to the PD0, PD1, PD2, PD3 and PD4 pins of port D of the programmable integrated circuit; and
   vi) a power supply.

2. The electronic device according to claim 1, wherein the programmable integrated circuit comprises an ATmega16A programmable integrated circuit.

3. The electronic device according to claim 1, wherein the converter is a digital-to-analog converter.

4. The electronic device according to claim 1, wherein the number of simple resistors is 16.

5. The electronic device according to claim 1, wherein the low consumption current amplifier comprises two inverting op amps.

6. The electronic device according to claim 1, wherein the screen-display is an LCD screen-display.

7. The electronic device according to claim 1, wherein the power supply is a +5v, +12v, and -12v power supply.

* * * * *